US012637792B2

(12) United States Patent
Wilhelms et al.

(10) Patent No.: US 12,637,792 B2
(45) Date of Patent: May 26, 2026

(54) MECHANICAL WOUND CLEANSING DEVICE

(71) Applicant: BSN Medical GmbH, Hamburg (DE)

(72) Inventors: Tim Wilhelms, Hamburg (DE); Arshi Annahit, Hamburg (DE); Patrick Schutz, Berlin (DE)

(73) Assignee: BSN MEDICAL GMBH, Hamburg (DE)

( * ) Notice: Subject to any disclaimer, the term of this patent is extended or adjusted under 35 U.S.C. 154(b) by 1567 days.

(21) Appl. No.: 16/979,995

(22) PCT Filed: Mar. 12, 2019

(86) PCT No.: PCT/EP2019/056161
§ 371 (c)(1),
(2) Date: Sep. 11, 2020

(87) PCT Pub. No.: WO2019/175172
PCT Pub. Date: Sep. 19, 2019

(65) Prior Publication Data
US 2021/0007764 A1 Jan. 14, 2021

(30) Foreign Application Priority Data

Mar. 13, 2018 (EP) ...................................... 18161465

(51) Int. Cl.
*D04H 3/10* (2012.01)
*A61B 17/54* (2006.01)
(Continued)

(52) U.S. Cl.
CPC ............... *D04H 3/10* (2013.01); *A61B 17/54* (2013.01); *D04H 11/00* (2013.01);
(Continued)

(58) Field of Classification Search
CPC ......... A61B 2017/00761; A61B 2017/320012; A61B 2017/00526; A61B 2017/320004;
(Continued)

(56) References Cited

U.S. PATENT DOCUMENTS 3,561,441 A * 2/1971 Lombardi ......... A61F 13/00017
602/44
4,542,739 A 9/1985 Schafer et al.
(Continued)

FOREIGN PATENT DOCUMENTS

CN 104401052 A 3/2015
DE 102007041630 A1 * 3/2009 ........... D04H 1/4382
(Continued)

OTHER PUBLICATIONS

European Patent Office, International Search Report, International Application No. PCT/EP2019/056161, mailed May 8, 2019 (6 pages).
(Continued)

*Primary Examiner* — Sarah A Long
*Assistant Examiner* — Lauren Dubose
(74) *Attorney, Agent, or Firm* — CANTOR COLBURN LLP

(57) ABSTRACT

The present invention relates to a mechanical wound cleansing device comprising a carrier layer and an abrasive loop system arranged above the carrier layer, whereby the loop system is an intermeshed fiber system which is intermeshed above the carrier layer and/or a loop system comprising highly and softly abrasive loops. The present invention further relates to a method of producing said mechanical wound cleansing device. The present invention finally relates to the use of said wound cleansing device for the abrasive removal of and cleansing of wounds, especially for venous leg ulcers, diabetic foot ulcers (neuropathic and
(Continued)

neuro-ischemic), arterial ulcers, mixed etiology ulcers, pressure ulcers or traumatic wounds.

23 Claims, 5 Drawing Sheets

(51) Int. Cl.
| | |
|---|---|
| *D04H 11/00* | (2006.01) |
| *A61B 17/00* | (2006.01) |
| *A61B 17/32* | (2006.01) |

(52) U.S. Cl.
CPC ................. *A61B 2017/0042* (2013.01); *A61B 2017/00526* (2013.01); *A61B 2017/00761* (2013.01); *A61B 2017/320012* (2013.01); *D10B 2331/04* (2013.01); *D10B 2509/00* (2013.01)

(58) Field of Classification Search
CPC ............ A61B 2017/0042; A61B 17/32; A61F 2013/00531; A61F 13/00008; A61F 13/00021; A61F 13/00987; A61F 13/36; A61F 13/00; D04H 3/10; D04H 11/00; D04H 3/147; D10B 2509/00; D10B 2331/04; D10B 2509/02; D10B 2403/00; D10B 2403/0114; D03D 1/00; D03D 15/283; D03D 15/292; D03D 27/00; D03D 15/49; D04B 1/04; D04B 1/22; D04B 21/04; D04B 21/165; D04B 21/20; B32B 5/06; B32B 5/073; B32B 2262/14152; Y10T 428/23936; Y10T 428/23957; Y10T 442/431; D02G 3/448; D02G 3/22; D02G 3/04; D02G 3/02; D02G 3/00; D02G 1/02; D02G 1/002
USPC ........................................................ 606/131
See application file for complete search history.

(56) References Cited

U.S. PATENT DOCUMENTS

| | | | |
|---|---|---|---|
| 4,570,461 | A | 2/1986 | Sawazaki |
| 4,984,570 | A | 1/1991 | Langen et al. |
| 6,063,049 | A | 5/2000 | Watkins |
| 7,273,648 | B2 * | 9/2007 | Morin .................... D03D 27/00 428/92 |
| 7,553,532 | B2 | 6/2009 | Turner et al. |
| 8,152,929 | B1 | 4/2012 | Perring |
| 9,713,553 | B2 | 7/2017 | Engl et al. |

| | | | |
|---|---|---|---|
| 2004/0265534 | A1 | 12/2004 | Curro et al. |
| 2005/0003140 | A1 * | 1/2005 | Zafiroglu ................ B32B 7/028 428/92 |
| 2005/0031828 | A1 * | 2/2005 | Yoshida ................... B08B 1/143 428/95 |
| 2010/0036334 | A1 | 2/2010 | Heagle et al. |
| 2010/0263152 | A1 * | 10/2010 | Wildeman .............. A47L 13/20 15/228 |
| 2010/0305489 | A1 | 12/2010 | Liu et al. |
| 2012/0046670 | A1 * | 2/2012 | Engl ........................ A61F 13/36 112/475.01 |
| 2013/0211307 | A1 | 8/2013 | Evans et al. |
| 2014/0249495 | A1 * | 9/2014 | Mumby .............. A61F 13/0206 604/385.01 |
| 2015/0150710 | A1 * | 6/2015 | Evans ................... A61F 13/069 602/6 |
| 2016/0317353 | A1 * | 11/2016 | Wang ................ A61F 13/01017 |
| 2016/0340815 | A1 * | 11/2016 | Kipke ............... A61F 13/00042 |
| 2017/0312141 | A1 | 11/2017 | Engl et al. |
| 2018/0311420 | A1 | 11/2018 | Cotton |

FOREIGN PATENT DOCUMENTS

| | | | | |
|---|---|---|---|---|
| DE | 2777662 | * | 9/2014 | ............ A61F 13/00 |
| EP | 2777662 | A1 | 9/2014 | |
| ES | 2547216 | T3 | 10/2015 | |
| JP | H01242195 | A | 9/1989 | |
| JP | H07330218 | A | 12/1995 | |
| WO | 2019073387 | A1 | 4/2019 | |

OTHER PUBLICATIONS

European Patent Office, Written Opinion of the International Preliminary Examining Authority, International Application No. PCT/EP2019/056161, mailed Feb. 21, 2020 (10 pages).

European Patent Office, International Preliminary Report on Patentability, International Application No. PCT/EP2019/056161, mailed Jun. 29, 2020 (26 pages).

Milin Patel et al., "Nonwoven Technology", Retrieved from the Internet: URL:https://web.archieve.org/web/20130903100356/https://textInfo.files.wordpress.com/2011/10/nonwoven-fabrics1.pdf#close, Sep. 3, 2013, pp. 1-54, XP055496201.

Office Action issued in Colombian Application No. NC2020/0010599; dated Jun. 26, 2023; 10 pages.

Colombian Application No. NC2020/0010599; Office Action with English Translation dated Jul. 11, 2022; 17 pages.

Brazilian Application No. 112020017977-9; Office Action with English translation dated Aug. 20, 2024; 8 pages.

European Application No. 25181354.9-1102 / 4589061; Extended European Search Report dated Sep. 19, 2025; 13 pages.

* cited by examiner

MECHANICAL WOUND CLEANSING DEVICE

CROSS REFERENCE TO RELATED APPLICATION

The present application is a U.S. national stage entry under 35 U.S.C. § 371 of, and claims priority to, International Application No. PCT/EP2019/056161, filed Mar. 12, 2019, which claims priority to European Application No. 18161465.2, filed Mar. 13, 2018, the disclosures of which are hereby incorporated herein by reference in their entireties.

FIELD OF THE INVENTION

The present invention relates to a mechanical wound cleansing device comprising a carrier layer and an abrasive loop system arranged above the carrier layer, whereby the loop system is an intermeshed fiber system which is intermeshed above the carrier layer and/or a loop system comprising highly and softly abrasive loops. The present invention further relates to a method of producing said mechanical wound cleansing device. The present invention finally relates to the use of said wound cleansing device for the abrasive removal of and cleansing of wounds, especially for venous leg ulcers, diabetic foot ulcers (neuropathic and neuro-ischemic), arterial ulcers, mixed etiology ulcers, pressure ulcers or traumatic wounds.

BACKGROUND OF THE INVENTION

Routine care of non-healing acute and chronic wounds often comprises either cleansing or debridement. Consequently, cleansing and debridement are a basic necessity to induce the functional process of tissue repair, which makes it a central medical intervention in the management of acute and chronic, non-healing wounds.

Furthermore, the natural cleaning abilities of the wound may be insufficient when there is a large trauma or when the patient is suffering from co-concomitant disorders such as venous disorders or diabetes. In these cases, considerable lengthening of the duration of the cleansing phase is observed leading to chronic wounds which are difficult to treat such as a leg ulcer.

For the cleansing purpose, several methods, devices and liquids have been used in the prior art. The use of cotton pads for wound cleansing is largely known and widely spread. Also known are surgical or hydro-surgical cleansing methods or the application of impulse wave therapy or ultrasound. The key requirements for a successful wound cleansing are that on the one hand any contaminants are removed as completely as possible and on the other hand any already beginning healing processes are not reversed by destroying and/or removing any newly formed granulation tissue.

The removal of debris and fibrinous tissue is commonly denoted by the term "assisted cleansing", as opposed to natural cleansing. Depending on the technique used, assisted cleaning can be classed as mechanical or surgical cleansing, enzymatic cleansing, autolytic cleansing or biological cleansing.

Surgical cleaning is a rapid technique that consists of cutting away the fibrinous tissue, either using a lancet, forceps, scissors or a Brock curette, or by means of sophisticated apparatus using water jets under pressure or laser excision. This technique is performed at the patient's bed or in the surgical environment depending on the severity of the wound. However, this technique is often painful and can lead to bleeding and sometimes even a hemorrhage. It is then traumatic for the patient. It commonly also requires prior analgesic medication, which increases the treatment time.

Mechanical wound debridement involves the use of dry gauze dressings, wet to dry gauze dressings, impregnated gauze/tulle dressings or a monofilament fibre pad to remove non-viable tissue from the wound bed.

Document U.S. Pat. No. 9,713,553 B2 proposes a wound cleansing assembly comprising protruding single fiber threads with beveled end surfaces. This material with the fibers having an beveled end surface has the disadvantage that it can cause skin irritations.

Hence, there is still a need for an improved mechanical wound cleansing device for efficient, safe and healing-supportive cleansing of acute and chronic wounds.

An aspect of the present invention thus is to provide a wound cleansing device which overcomes at least one of the above-described disadvantages.

SUMMARY OF THE INVENTION

In one aspect, the present invention provides a wound cleansing device comprising a carrier layer and a loop system made from fibers, whereby the loop system is arranged on at least on one side of the carrier layer and protrudes from the carrier layer, and wherein the loop system is an intermeshed fiber system, which is intermeshed above the carrier layer.

The wound care product of the present invention has several advantages over wound care products known in the prior art.

The protruding loops enable efficient abrasive properties, the strength of which can be easily controlled by manually increasing the pressure on the wound to be treated. It has been shown that this specific loop architecture with two different fiber loops or an intermeshed op system still result in a soft appearance of the overall product keeping the granulation tissue largely intact and reduces the pain sensation during treatment.

Hence, the use of protruding fiber loops largely reduces the risk for skin irritation. This is given by the loop formation as such in contrast to sharp fiber endings and also by the fact that the fiber loss in loops is strongly reduced.

By representing an intermeshed loop fiber system with meshes within or below the carrier layer, the wound cleansing device can not only absorb or collect the removed material but this material is also held in the meshes of the loops and thereby prevents the recontamination of the wound. This is supported by the enhanced property of the wound cleansing device to absorb liquids as results of capillary effects of the loops. As a consequence, the mixture of solid particles and liquids which is taken up by the cleansing device from the wound is rapidly dewatered by capillary liquid removal and the remaining solid particles adhere to the fibers/filaments.

Representing a textile fabric, a broad spectrum of textile and fiber materials allows the selection of the optimal material with regard to costs, processability, abrasive properties, softness, liquid absorbance.

By using two different fiber loops, namely the highly abrasive loops and the softly abrasive loops, the cleansing device can be used for a broad spectrum of wounds. It thereby can fulfil the two separate functions, namely the classical wound cleaning (removal of loose metabolic waste or foreign material) and the debridement as the removal of bioburden from the wound bed and liberation of wound edges as well as of peri-wound skin.

The loop architecture can be adopted so that, at first, the softly abrasive loops will contact the wound surface and, if required, upon higher pressure the shorter and thereby recessed strongly abrasive loops will interact with the wound surface.

The present wound cleansing device can be further equipped with a liquid absorbing layer. In a form of a pre-soaked liquid releasing layer, the released liquid can support the wound cleansing by actively draining any material out of the wound.

The wound cleansing device can be provided with additional layers such as, e.g., a covering layer as a liquid impermeable layer, preventing the contamination of the user and the environment.

As a textile fabric the wound cleansing device can be easily sterilized and stored for its safe use in wound cleansing and wound debridement.

Since the wound cleansing device of the present invention is based on known textile materials, it can be easily produced in a cost-efficient manner.

Due to its specific properties, the wound cleansing device has the capability to achieve clinical benefits such as increased quality of life of the patient, fewer odours, improved microcirculation, normalised biochemistry including normalising the matrix metallo-proteinase (MMP) balance, decreased access of moisture and stimulated wound edges.

In sum, the wound cleansing device of the present invention enables a rapid, safe and easy-to-use wound treatment with limited pain for the patient.

DETAILED DESCRIPTION OF THE INVENTION

According to one embodiment of the present invention, the loop system is intermeshed within or below the carrier layer. The intermeshed loop system may be generated by stitch-bonding. The stitch-bonding process involves bonding yarn or filament layers, webs or flat substrates by means of a system of stitches. The Textile Institute defines stitch bonded or sew-knit fabric as a multi-component fabric, one component of which is a series of interloped stitches running along the fabric length. Hereby, a multiplicity of stitching yarns or filaments is passed repeatedly in stitching relation through a substrate layer in closely spaced rows so as to form a coordinated arrangement of surfaces stitches and/or protruding loops and the substrate. Various types of machines are available for carrying out this process such as Maliwatt, Malivlies or Malipol. Further techniques include Voltex, Kunit, Multiknit, and Intor. In the Maliwatt stitch bonding method, a fibrous web as carrier layer is bonded without threads but the fibers are pulled out of the layer to create bonding bundles. In the Malivlies method, the fibrous web as carrier layer is bonded by a system of threads. In the Malipol method the bonding creates loops on the surface.

The Maliwatt system consists of the following components:

Stitch bonding unit with drive system for the working elements;
Web feed system;
Yarn feeding and monitoring systems;
Take-up of stitch bonder fabric and fabric storage or plaiting; and
Cutting and tearing unit, and a machine control and drive system.

The Malipol stitch bonding systems have the following main elements:

Pile yarn;
A carrier layer (ground fabric);
Stitch bonding head; and
Fabric take-down and batching.

In one embodiment of the present invention, the loop system is arranged on one side of the carrier layer, and protrudes from the carrier layer, so that the wound cleansing device has a carrier layer with a first side carrying said loops and a second side without loops.

According to one embodiment of the present invention, the loop fiber system represents a first external surface of the wound cleansing device configured to face the wound. It can therefore be regarded as the wound contact layer and wound interaction layer.

According to one embodiment of the present invention, the loop system comprises highly and softly abrasive loops. Thus, the system comprises to different classes of loops differentiating by their abrasive behaviour as defined by certain fiber characteristics.

According to one embodiment of the present invention, the highly abrasive loops are built from fibers selected from the group consisting of:

(a) Multifilament-yarns with a thickness between 167 and 1500 dtex, and preferably between 500 and 1500 dtex, which are made from microfilaments. Due to the increased thickness of these yarns, they have an increased abrasive capacity although they are built from fine microfilaments;

(b) Core-twisted yarns having a monofilament core surrounded by finer filaments, being preferably microfilaments; and (c) Monofilaments with a thickness between 1 and 300 dtex, and preferably more than 3.1 dtex, or having a diameter between 0.05 and 0.5 mm.

In one embodiment of the present invention, the highly abrasive loops are evenly distributed over the surface area and thereby form a closed surface without discrete gaps. In this form, they show an excellent abrasive efficacy.

In one embodiment, the highly abrasive loops are generated by a stitch-bonding technique such as generated by the Malipol machine.

According to one embodiment of the present invention, the softly abrasive loops are built from fibers selected from the group consisting of:

(a) Textured yarns such as chenille with a thickness of less than 120 dtex;

(b) Flock threads consisting of a ground thread and microfilaments arranged transversely to the ground thread;

(c) Yarns with a thickness of less than 600 dtex which are made from microfilaments; having preferably a thickness between 76 to 334 dtex, and more preferably between 150 to 200 dtex, and specifically of 167 dtex;

(d) Monofilaments with a thickness of less than 1 dtex; and whereby the loop system may comprise an intermeshed fiber system according to one aspect of the present invention.

In one embodiment of the present invention, the softly abrasive fibers are generated by a combination of the Maliwatt system with pile and the Malipol system.

In one embodiment of the present invention, the softly abrasive loops are distributed in a way that areas of softly abrasive fibers are separated by a fine gap. These gaps support the uptake of particles which are detached by the cleansing process. The gaps may have a stripe configuration.

As cleansing-improving stripes, these elongated gaps are also denominated as "cleansing lanes". The rectangular areas may be separated by orthogonally oriented lanes and thus form a grid of rectangular loop areas interspersed by the cleansing lanes. According to one embodiment, a system is provided whereby the orthogonal oriented lanes may consist of lanes in longitudinal direction combined with lanes in transverse direction.

In a further embodiment of the present invention the intermeshed loop system comprises a least two types of threads, a sewing thread and a pile thread being a highly abrasive or softly abrasive thread.

In this system, the pile threads form the loops and penetrates the carrier, whereby the sewing thread will represent the visible meshes at the reverse side of the carrier.

In the stitch-bonding system, the meshes are worked into the carrier material so that the meshes will be visible on the reverse side. On the front side, the mesh bar is formed as a pile loop.

In one embodiment of the present invention, the sewing thread has a thickness between 33 and 167 dtex, and preferably of 76 dtex.

In one embodiment of the present invention, the yarn can be of any type such as parallel or cabled yarn, twisted yarn, plied yarn, texturized yarn or core spun yarn. For the softly abrasive fiber loops, the use of a cabled/parallel yarn is contemplated giving rise to soft and bushy loops. For the highly abrasive fibers, core spun threads or twisted yarns are contemplated showing higher stiffness.

In one embodiment, the loop fiber system covers at least 50% of the total surface of the carrier layer, preferably at least 75% of the surface, more preferably at least 85% of the surface, and most preferably at least 90% of the surface of the carrier layer.

The loop system of the present invention has preferably a stitch density between 3.5 F/25 mm and 22 F/25 mm, with a more preferred stitch density between 12 F/25 mm and 18 F/25 mm.

This is equivalent to a mesh density of between 28.000 and 1.760.000 meshes/m² or in the more preferred embodiment of between 400.000 and 900.000 meshes/m².

In one embodiment of the present invention, the strongly abrasive loops of the wound cleansing device have a height above the carrier layer which is less than the height of the softly abrasive loops. Consequently, the softly abrasive loops will contact in the first instance the wound surface and will perform the classical wound cleaning and the removal of rather loosely attached bioburdening material. If required, a higher pressure can be exerted so that the shorter, thereby recessed, strongly abrasive loops will interact with the wound surface and perform a more stringent debridement for removal of firmly attached material.

According to one embodiment of the present invention, the strongly abrasive loops and the softly abrasive loops could be arranged in multiple ways. Exemplary arrangements, without being limited to them, include the following:

The strongly abrasive loops and the softly abrasive loops are stacked upon each other. Thereby a multi-functional fabric is created in a very compact manner.

The strongly abrasive loops and the softly abrasive loops can be arranged side by side, so that both loop types have direct contact to the wound site.

The strongly abrasive loops form a pile loop area which is separated from a pile loop area formed by the softly abrasive loops. As in the side-by side design type, bot loop types have a direct contact, whereby the multitude of fiber loops in each area increase their specific activity.

The carrier layer and/or the loop-forming fibers of the wound cleansing device can be made from natural, semi-synthetic or synthetic fibers. Hereby, one of ordinary skill in the art can select the fiber material from a broad range of known textile material and according to the specific cleansing requirements.

In one embodiment of the present invention, the natural fibers are cellulose fibers such as cotton fibers.

When using semisynthetic fibers, viscose fibers or acetate fibers may be used.

In the field of the synthetic fibers, a polymer selected from polyester, polyacrylonitrile (PAN), polyethylene, polypropylene or polyamide may be used.

In one embodiment of the present invention, the loop fiber system, and possibly also the carrier layer, are made from a hydrophilic fibers or filaments which may assist in the removal of excessive exudate from the wound. For the case that a further proximally located liquid absorbing layer is present, the hydrophilic loop fiber system and carrier layer assist in the transport of the exudate to the liquid absorbing layer.

The fibers can suitably be bi-component fibres. Several architectures can be hereby used such as a sheet/core architecture, a side-by side architecture, an island-in-the-sea architecture, or a wedge-pie architecture.

The fibers or filaments can have a round cross-section. However, alternative cross-sections, such as triangular, tri-lobal, polygonal, scalloped oval, lobular with lengthwise striations, dog-bone, concertina, star, Y-shaped, collapsed tubes, square with voids, cruciform, ribbon, bean, or hex-achannel can also be used.

The carrier layer of the device can comprise or consist of a nonwoven fabric, a woven fabric, a net or a knitted fabric.

In one embodiment, the carrier layer is a non-woven with the advantage of being a cost-efficient uniform structure representing a good support layer for the production of the loop fiber system on top of it which thereby will reinforcing the non-woven carrier layer.

In a further embodiment, the non-woven comprises or consists of hydrophilic fibers in order to facilitate the absorption of aqueous liquids such as wound exudate or irrigation fluid.

In an exemplary embodiment of the present invention, the carrier layer is a non-woven having a content of from 5% to 35% of low melt fibers most preferably provided as bicomponent fibers. Examples for low melt Bicomponent fibers are CoPES or Bico fibers.

In a further embodiment, the carrier layer is a non-woven which is reinforced by seams of a further thread which preferably have a stitch density of 3 to 5 stitches/cm.

The intermeshed loop fiber system may comprise or consist of a knitted or stitch bonded structure. By way of non-limiting example, suitable knitting patterns include warp knitting, tricot or atlas.

In one embodiment, the intermeshed loop fiber system has a rib or square optic which further increase the surface of the loop fiber system and thereby enhances the ability to sequester the removed material.

In one embodiment of the present invention, the wound cleansing device further comprises a liquid absorbing layer which can absorb excessive wound exudate from the wound or alternatively as s pre-soaked layer can release an irrigation fluid to the wound thereby enhancing the cleansing and/or debridement.

Accordingly, the liquid absorbing layer is suitably arranged on the opposite side of the carrier layer with regard to the loop fiber system.

Said liquid absorbing layer may be positioned directly on top of the carrier layer so that the liquids can more easily be absorbed from the wound site or alternatively released from the absorbing layer to the wound site.

The liquid absorbing layer of the present invention absorbs the liquid released by the wound which is mainly the wound exudate. As the most proximal layer with regard to the carrier layer and the loop fiber system of the present invention, it triggers a flow of the wound exudate through the two other structures. By absorbing the deleterious wound exudate and meanwhile providing a moist wound climate, this layer promotes the process of wound healing.

The liquid absorbing layer of the wound care article can be made from various medically safe materials, such as open-cell foam plastic, gel or textile.

In one embodiment of the present invention, the liquid-absorbing layer comprises, consists essentially of or consists of at least one absorbent material selected from the group consisting of polymer foams, sponges, hydrocolloids, hydrogels and hydrophilic polymers such as superabsorbent polymers.

In one embodiment, it consists of at least one layer of a hydroactive fiber or another textile material and/or comprises hydroactive polymers.

Hydroactive polymers can be selected from the list consisting of superabsorbent polymers, alginates, hydrogel nanoparticles and combinations thereof.

The term "hydroactive polymers" is to be understood hereinafter as referring to polymers capable of binding large amounts of liquid. Said polymers preferably comprise superabsorbent substances comprising polyacrylates, modified cellulose and/or alginates.

In one embodiment of the present invention, the upper liquid-absorbing layer further comprises at least one antimicrobial active compound, preferably selected from the group consisting of bacteriocin like inhibitory substance (BLIS), silver or copper based compound, biguanide salt like polyhexamethylbiguanide (PHMB), chlorhexidine, phenol derivatives, such as thymol and eugenol, chlorophenol and chlordiphenyl ether.

In one embodiment, the liquid-absorbing layer comprises or consists of a non-woven, a foam or a textile composite such as a laminate with different layers.

In one embodiment, the liquid absorbing laser consists of an open-celled foam which more preferably is a reticulated foam exhibiting high porosity and large surface area. As a porous foam layer, it can both absorb and release liquids very rapidly and with similar efficacy. As a consequence, it can be provided as a foam which is presoaked with an irrigation fluid, and exerting pressure on the device the irrigation fluid is pressed out of the foam into the wound, soften the wound and thereby facilitate the cleansing and debridement process. As a squeezed (partially) emptied foam, it can then absorb the debris-enriched irrigation fluid together with excessive wound exudate.

Several types of irrigation fluids for the liquid absorbing layer are known in the prior art. By way of non-limiting example, suitable irrigation fluids include Ringer solution, normal saline, solution comprising undecylenamidopropyl-betain and Polyhexanide; an aqueous povidone iodine solution, an aqueous hydrogen-peroxide solution, or an aqueous sodium hypochlorite solution (so called Dankin's solution).

In a further embodiment, the liquid absorbing laser consists of an open-celled foam which is preferably made of polyurethane, polyacrylamide, polyethylene.

The wound cleansing device can be provided with additional layers such as, e.g., a covering layer as a liquid impermeable layer, preventing the contamination of the user and the environment and also the penetration of dirt and bacteria into the wound cleansing device or even the wound.

This aim can be achieved by, for example, applying a fluid impermeable continuous protective film (hereinafter also referred to as backing film) as cover layer, whereby in a practical manner the backing film is water vapour-permeable. This layer which, as described above, should typically be impermeable to bacteria, adjoins the distal surface of liquid-absorbing layer. In one embodiment of the present invention, the film is only bound to the distal surface of the absorbing layer in a manner so that the film penetrate into the pores, cells or other intermediate spaces. The cover layer can be transparent to allow the level of filling or moisture in the wound cleansing device or the status of the wound to be assessed without having to remove the dressing. The cover layer can be filled with coloring agents. In general the film has a thickness of 10-500 μm and typically 15 to 45 μm, whereby film thicknesses of 30± micrometers are used in particular.

Films of this type are known from the prior art and comprise, for example, polyethylene-, polypropylene-, polyester-, polyurethane- or polyimide-based films.

Polyurethane-based films may be used, such as a polyurethane film supplied by Exopack Advanced Coatings (Wrexham, UK) under the product name INSPIRE®, or elastomer polyesters or mixtures of polyurethane with polyesters and/polyvinyl chloride and polyether amide block copolymers. Alternatively, the backing layer can be a water-repellent and water vapour-permeable polyurethane foam with essentially closed cells, such supplied, for example, by Scapa (Greater Manchester, UK) under the product name Medifix.

For the purposes of the present application according to one embodiment, a polyurethane film is used as these films have good elastic properties and, in particular, exhibit form fitting properties as well as a high level of stretchability.

In a further embodiment, the wound cleansing device comprises proteolytic enzymes to hydrolyze peptide bonds, in order to facilitate the removal of non-viable tissue from the wound.

By way of non-limiting example, suitable proteolytic enzymes include fibrinolysin, DNA from bovine pancreas, krill multienzyme complex, collagenase Clostridiopeptidase A from Clostridium histolyticum, Bromelain enzyme complex, streptokinase, streptodornase or sutilain.

In a further embodiment, the wound cleansing device comprises silver or copper as antimicrobial agents. These metals can be included in the form of pure silver or copper filaments/fibers or by synthetic fibers which are coated with a copper or silver coating. The copper/silver might be included in one or more of the substructures of the device, namely in the liquid absorbing layer, the carrier layer, the loop fiber system, or the intermeshed fiber system.

The dimension of the surface area of the wound cleansing device may be selected according to the size of the wound but restricted to the possibility to sue it as a manual device. Typically, a wound cleansing device of the present invention may have a surface area of from 25 cm² to 400 cm², and particularly of from 25 cm² to 200 cm², such as 100 cm². Also the shape of the wound cleansing device according to the present invention may vary with respect to the wound to be treated, and the present invention encompasses, for example, rectangular, square-, circle- or oval-shaped wound cleansing device. For example, the wound cleansing device may have a rectangular shape with rounded corners as depicted in FIG. 2B.

In one embodiment of the present invention, the wound cleansing device further comprises a handle, a grip, a hand strap, or a pocket.

In another aspect, the present invention according to an exemplary embodiment provides a method for manufacturing the wound cleansing device comprising the following steps:

(a) provision of a nonwoven which may be made of Polyester with 100-200 g/m²;

(b) generating a loop system arranged on the nonwoven of step (a) by using a stitch bonding process containing a pile thread and a sewing thread;

(c) heating of the structure generated in (b) to activate the low melt fibers of the carrier layer;

(d) optionally adhering a foam layer on the back side of the carrier layer;

(e) optionally laminating the back side of the carrier layer of the structure generated in (c) or the surface of the foam layer as introduced in step (d); and (f) optionally cutting and sealing the device by ultrasonic sealing.

In one embodiment of the present invention, the wound cleansing device is produced by stitch bonding machine which is the combination of a Maliwatt machine with pile thread arrangement and a Malipol machine having at least two guide bars. Hereby, the two different pile thread materials (i.e., softly and strongly abrasive) are processed as one thread system with one of the guide bars. Hereby, the two production methods, being preferably Maliwatt with pile and Malipol can be integrated within one machine.

In order to generate cleansing lanes in longitudinal direction, a dedicated thread feeder in both guide bars may be used.

Cleansing lanes in transverse direction can be generated by patterning drives, whereby different weave patterns can be specified such as tricot-fringe or plain weave-fringe.

In a further aspect, the present invention relates to the use of the wound cleansing device of the present invention for the removal of necrotic material, eschar, devitalised tissue, serocrusts, infected tissue, hyperkeratosis, slough, pus, haematomas, foreign bodies, debris, bone fragments or any other type of bioburden from a wound with the objective to promote wound healing.

An exemplary process of wound cleansing by use of the cleansing device of the present invention encompasses the following steps:

1. Soaking or moistening the cleansing device with a cleansing solution.

2. Wiping or rubbing the wound areal with the cleansing device as prepared in step 1 with the intermeshed layer facing the wound site.

3. In case the loops of the cleansing device are saturated with wound debris but further wound cleansing is required, repeat steps 1 and 2 by using a new cleansing device.

In one embodiment of the present invention, the use of the wound cleansing device includes also the liberation of wound edges and/or the liberation of peri-wound skin and thereby facilitates a subsequent wound closure.

In one embodiment, the wound cleansing device is used for the treatment of venous leg ulcers, diabetic foot ulcers (neuropathic and neuro-ischemic), arterial ulcers, mixed etiology ulcers, pressure ulcers or traumatic wounds.

In a further aspect, the present invention provides an arrangement comprising at least one wound cleansing device of the present invention packaged within a sealed package.

In one embodiment, the sealed package is an air-tight package which is more preferably a plastic package.

The at least one wound cleansing device may be packaged in a sterile fashion.

BRIEF DESCRIPTION OF THE DRAWINGS

These and other aspects of the present invention will be apparent from and elucidated with reference to the embodiments described hereinafter.

The present invention will now be described, by way of example, based on embodiments with reference to the accompanying drawings. In the drawings:

FIG. 3 shows a principal sketch of a wound cleansing device 1 in cross section with areas 5 of fiber loops arranged on the carrier layer 2 and a liquid absorbing layer 6 arranged on the opposite site of the carrier layer and overlaid by a liquid impermeable layer 7.

In the Figures, like numbers refer to like objects throughout. Objects in the Figures are not necessarily drawn to scale.

DETAILED DESCRIPTION OF EMBODIMENTS

Various embodiments of the present invention will now be described by means of the Figures.

Figure 1:
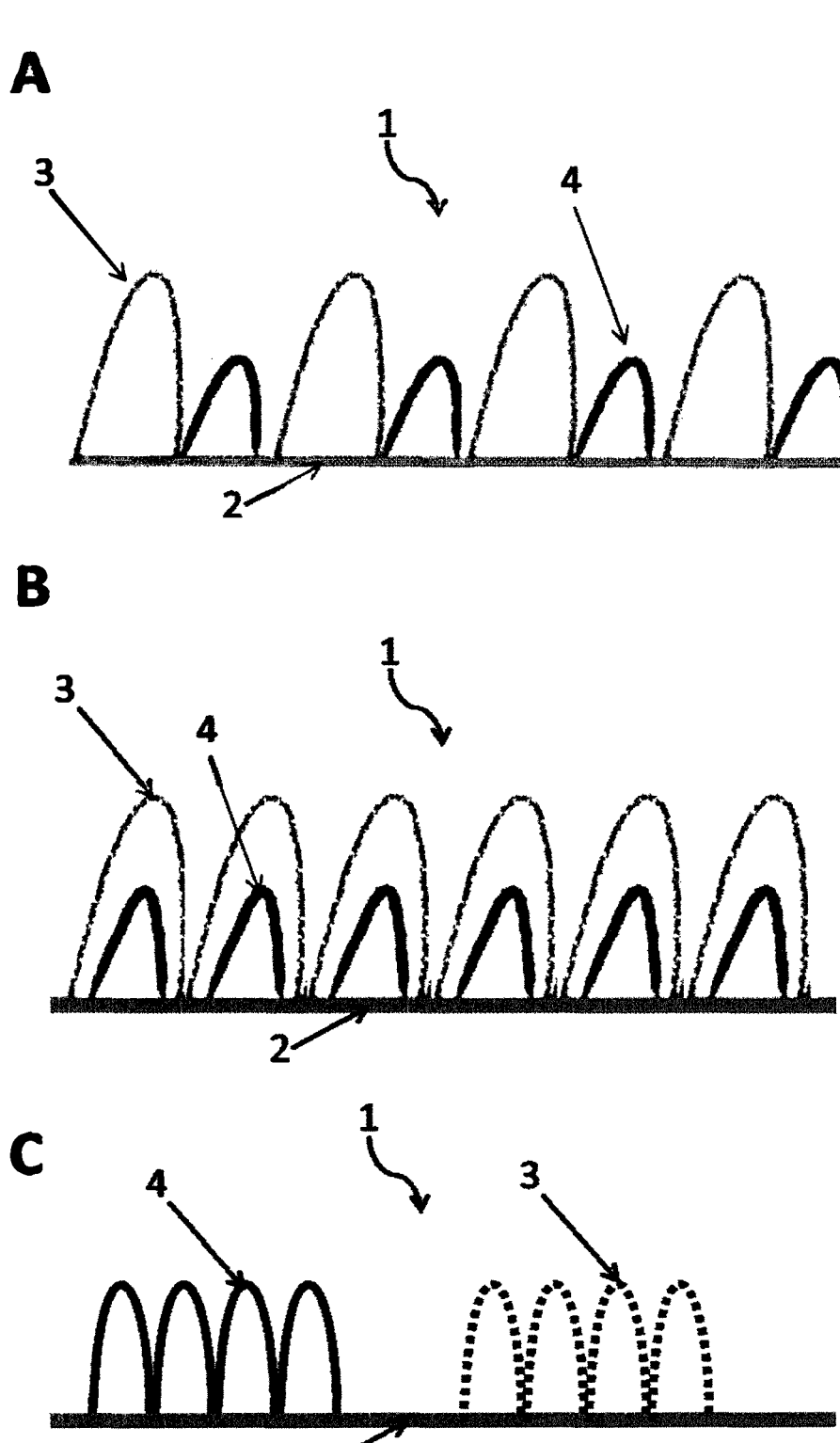
FIG. 1 shows a principal sketch of the wound cleansing device 1 according to a first embodiment in cross section with fiber loops of bulky microfilaments fiber loops 3 as softly abrasive fiber loops and monofilament loops 4 as highly abrasive fiber loops arranged on a carrier layer as alternating loop arrangement (A) as superimposed loops (B) or as discrete areas of highly and softly abrasive loops (C).

FIG. 1 shows in (A) a wound cleansing device 1 with a carrier layer 2 having on its upper side an alternating mixture of softly abrasive fiber loops 3 and highly abrasive fiber loops 4 in a side-by-side configuration. In the embodiment shown in (B), the softly abrasive fiber loops 3 are arranged below the highly abrasive fiber loops 4. The wound cleansing device 1 according a further embodiment as shown in (C) has a carrier layer with areas of softly abrasive fiber loops separated from areas of highly abrasive fiber loops.

Figure 2:
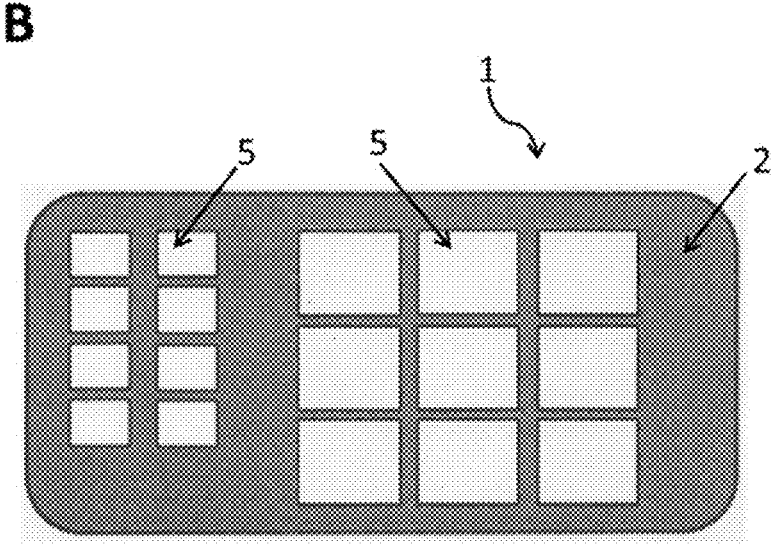
FIG. 2 shows in (A) the line drawing of a wound cleansing device 1 with rows of intermeshed fiber loops from above, and in (B), a principal sketch of a wound cleansing device with areas 5 of fiber loops arranged on the carrier layer 2.
Figure 4:
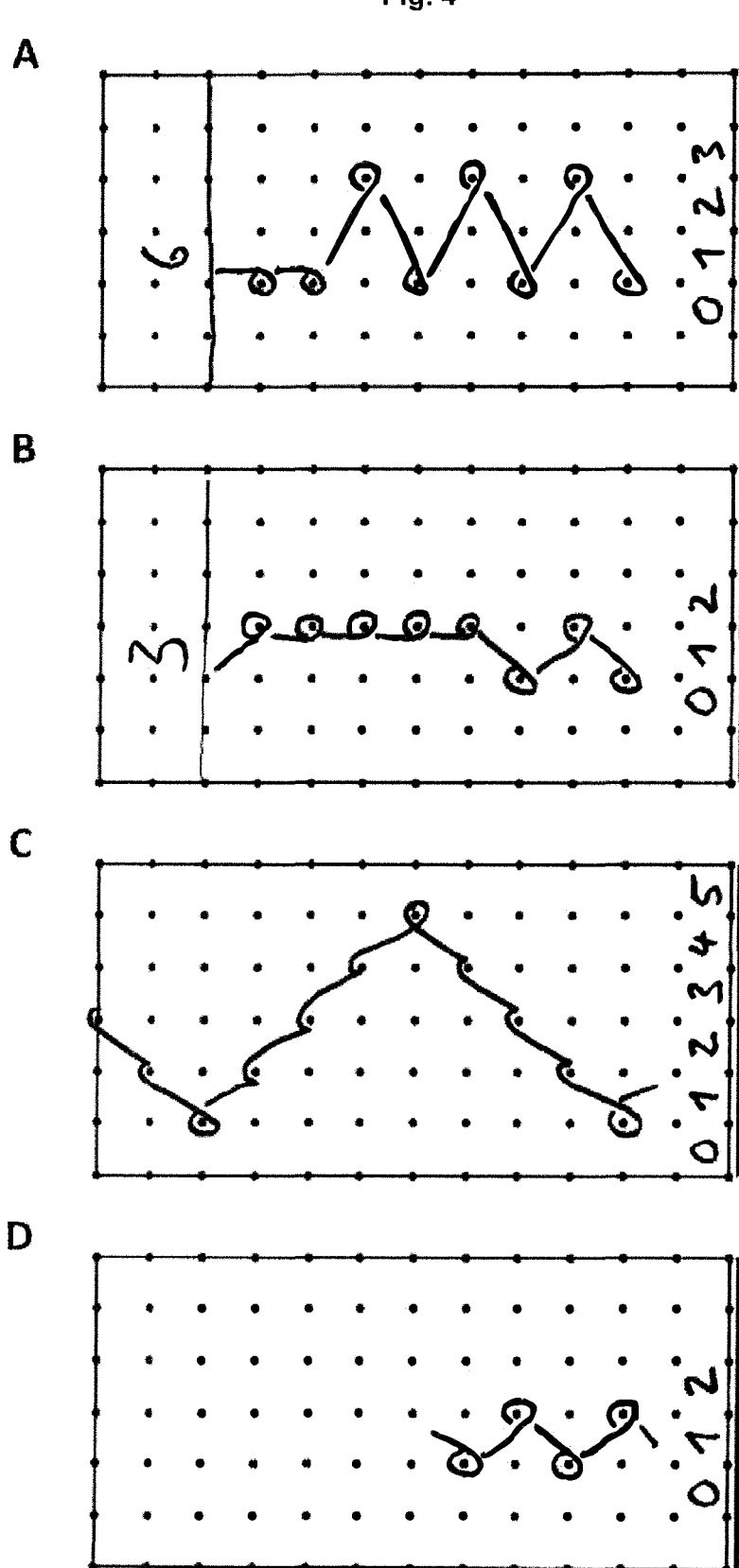
FIG. 4 shows four possible weave patterns for the pile threads as lapping diagrams with two different tricot-fringes in (A) and (B), a satin weave in (C) and a closed tricot weave in (D).
Figure 5:
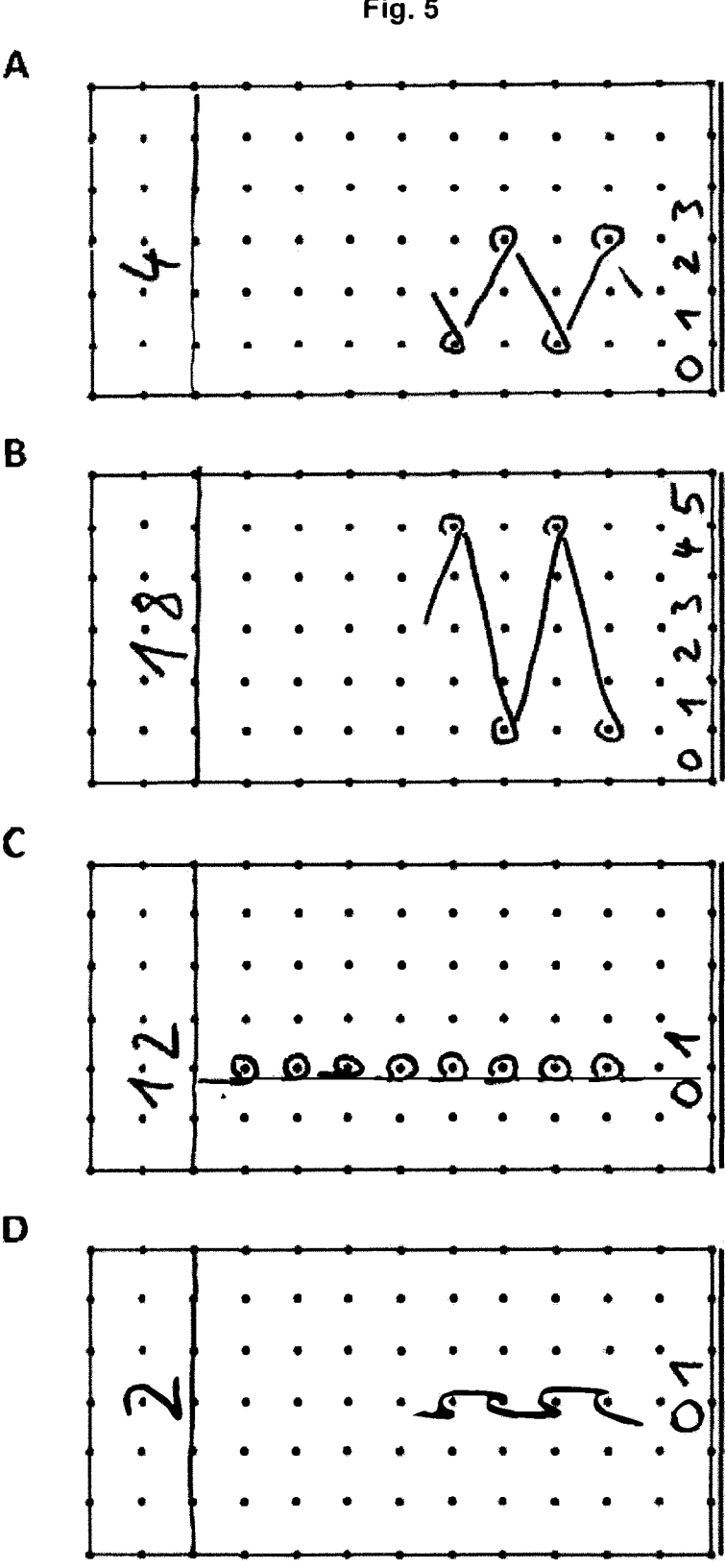
FIG. 5 shows two possible weave patterns for the pile threads as lapping diagrams in (A) and (B) with plain weave in (A) and a velvet lapping in (B), and furthermore two possible weave patterns for the ground threads as lapping diagrams in (C) and (D) with closed fringe in (C) and open fringe in (D).

FIG. 2 shows in (A) a line drawing of a wound cleansing device according to one embodiment of the present invention. The softly abrasive loops build a dense network of bushy fiber loops arranged in stripes with separating loop-free lanes, the so called "cleansing lanes". The mesh-like structures which are seen in the cleansing lanes are generated by the sewing threads strengthening the non-woven carrier layer. The wound cleansing device 1 shown in (B) has a rectangular carrier layer with rounded corners. The carrier layer is equipped on the left side with an area of softly abrasive fibers build up by several rectangular fiber loop-carrying sub-areas divided by cleansing lanes and on the right side with an area of highly abrasive fibers build up by several rectangular fiber loop-carrying sub-areas divided by cleansing lanes.

Figure 3:
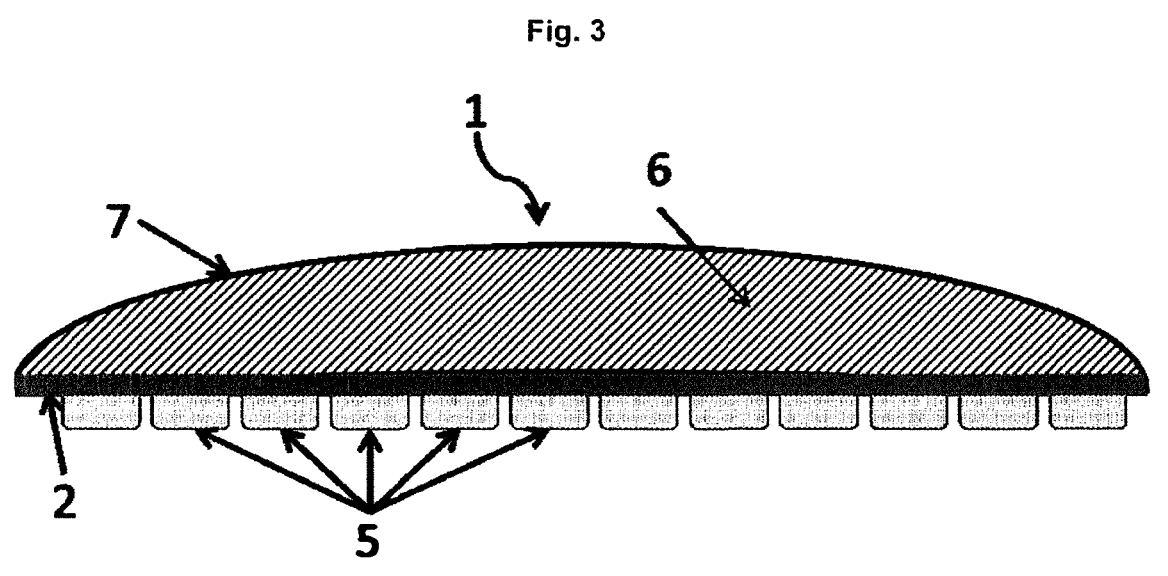

FIG. 3 shows a further embodiment of the cleansing device 1 with a carrier layer 2, exhibiting on the lower side (i.e., oriented towards the wound) several separated areas of abrasive fiber loops and on the upper side a liquid absorbing layer 6 with a liquid impermeable layer 7 as top layer.

While the present invention has been illustrated and described in detail in the drawings and the foregoing description, such illustration and description are to be considered illustrative or exemplary and not restrictive.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality of elements or steps. The mere fact that certain measures are recited in mutually different dependent claims does not indicate that a combination of these measures cannot be used to advantage.

Any reference signs in the claims should not be construed as limiting the scope thereof.

Definitions

According to one embodiment of the present invention, a "loop system" is a multitude of fiber or filament loops arranged on the carrier system and protruding from the carrier system in a predetermined regular way.

As used herein, a "monofilament" is defined as a single untwisted synthetic filament.

The term "yarn" is defined as a long, continuous length of interlocked fibers. These fibers could be either natural, semi-synthetic fibers or filaments. The interlocking can be by twisting, plying or grouping together.

The "microfilaments" referred to herein are defined as continuous strands having a diameter in the region of about 17 to 20 µm or a linear density between 0.3 and 1.0 dtex. The term dtex means decitex and is a unit expressing the linear density as the mass in grams of a 10,000 meter length of one filament. An alternative means of expressing the definition of a microfilament may be by reference to fiber thickness, which is generally expressed as a fiber diameter.

The term "nanofilaments" which is synonymous with the term "super-microfilaments" denotes to filaments with cross-sectional dimensions of less than 1 µm or a liner density of less than 0.3 dtex.

In the context of the present invention, the term "low melt fibers" is defined as fibers having a melting point between 110° C. and 180° C.

The term "cleansing" as used in the context of the present invention according to one embodiment encompasses the debridement as well as the classical cleaning.

The term "debridement" as used herein refers to deeply removing adherent, dead or contaminated tissue from a wound and must be clearly separated from the act of classical cleaning, defined as the removal of dirt (loose metabolic waste or foreign material). Furthermore, debridement does not encompass revision of a wound, resection of functional tissue or amputation. Thus, debridement is defined as the act of removing necrotic material, eschar, devitalised tissue, serocrusts, infected tissue, hyperkeratosis, slough, pus, haematomas, foreign bodies, debris, bone fragments or any other type of bioburden from a wound with the objective to promote wound healing.

Debridement is sometimes referred to as a form of wound bed preparation; however, it has become clear that not only the wound bed but also the wound edges and the peri-wound skin are important for the successful healing of a wound. Hence, the present definition of the term "debridement" does not only refer to the removal of bioburden from the wound bed, but also the liberation of wound edges as well as of peri-wound skin.

The terms "proximal" and "distal" are used in the present invention to define the location of certain structures and especially layers in relation to the wound site. Proximal denotes to structures which are closer to the wound site, and distal to structures which are situated further away from the wound site.

The term "non-woven" is herein defined as sheet or web structures bonded together by entangling fiber or filaments mechanically, thermally or chemically. They are flat or tufted porous sheets that are made directly from separate fibers or filaments. Non-woven are not made by weaving or knitting and do not require converting the fibers to yarn.

What is claimed is:

1. A wound cleansing device, comprising:
a carrier layer and a loop system made from fibers, wherein the loop system is arranged on at least one side of the carrier layer and protrudes from the carrier layer, wherein the loop system is an intermeshed loop fiber system which is intermeshed within or below the carrier layer,
wherein the loop system comprises highly abrasive loops and softly abrasive loops, and
wherein the intermeshed loop fiber system comprises a stitchbonded structure,
wherein the highly abrasive loops are made from core-twisted yarns having a monofilament core surrounded by filaments that are finer than the monofilament core, and
wherein the wound cleansing device is structured to clean a wound.

2. The wound cleansing device according to claim 1, wherein the filaments finer than the monofilament core are microfilaments.

3. The wound cleansing device according to claim 1, wherein the softly abrasive loops are made from fibers selected from the group consisting of:
(a) textured yarns with a thickness of less than 120 dtex;
(b) flock threads consisting of a ground thread and microfilaments arranged transversely to the ground thread;
(c) yarns with a thickness of less than 600 dtex which are made from microfilaments or a thickness between 76 to 334 dtex, or a thickness between 150 to 200 dtex, or a thickness of 167 dtex;
(d) monofilaments with a thickness of less than 1 dtex.

4. The wound cleansing device according to claim 1, wherein the softly abrasive loops are stacked upon the highly abrasive loops.

5. The wound cleansing device according to claim 1, wherein the carrier layer and/or the fibers of the loop system are made from natural, semi-synthetic or synthetic fibers.

6. The wound cleansing device according to claim 1, whereby the carrier layer is selected from the list consisting of:
a nonwoven fabric;
a woven fabric;
a net; and
a knitted fabric;
wherein the nonwoven fabric has a content of 5% to 35% low melt fibers or bicomponent fibers.

7. The wound cleansing device according to claim 1, further comprising a liquid absorbing layer selected from a list consisting of non-woven, foam or a textile composite.

8. The wound cleansing device according to claim 7, whereby the foam is made from one of the following polymers: polyurethane, polyacrylamide, Polyethylene.

9. The wound cleansing device according to claim 7, whereby the liquid absorbing layer is soaked with an aqueous liquid selected from Ringer solution, normal saline, solution comprising undecylenamidopropyl-betain and Polyhexanide.

10. The wound cleansing device according to claim 1, further comprising a top layer of liquid impermeable layer made of a material selected from polyethylene, polypropylene, polyester or polyamide.

11. The wound cleansing device according to claim 1, further comprising a handle, a grip, a hand strap, or a packet.

12. A method for manufacturing the wound cleansing device according to comprising the following steps:
(a) provision of a nonwoven;
(b) generating the loop system arranged on the nonwoven of step (a) by using a stich bonding process containing a pile thread and a sewing thread; and
(c) heating of the loop system generated in (b) to activate low melt fibers of the carrier layer.

13. A use of the wound cleansing device according to claim 1, in one or more of the following:
(a) removal of necrotic material, eschar, devitalised tissue, serocrusts, infected tissue, hyperkeratosis, slough, pus, haematomas, foreign bodies, debris, bone fragments or any other type of bioburden from the wound with an objective to promote wound healing;
(b) liberation of wound edges and/or peri-wound skin; and
(c) treatment of venous leg ulcers, diabetic foot ulcers (neuropathic and neuro-ischemic), arterial ulcers, mixed etiology ulcers, pressure ulcers or traumatic wounds.

14. An arrangement comprising at least one wound cleansing device according to claim 1, packaged within a sealed package, whereby the sealed package is an air-tight plastic package and the at least one wound cleansing device is packaged in a sterile fashion.

15. The method of claim 12, wherein the nonwoven is made of Polyester with 100-200 g/m$^2$.

16. The wound cleansing device according to claim 1, wherein the highly abrasive loops form a first pile loop area that does not include any of the softly abrasive loops, the softly abrasive loops form a second pile loop area that does not include any of the highly abrasive loops, and the first pile loop area and the second pile loop area are separated by an area that does not include any of the highly abrasive loops or the softly abrasive loops.

17. The wound cleansing device of claim 3, wherein the textured yarns comprise chenille.

18. The wound cleansing device according to claim 1, wherein the highly abrasive loops have a height above the carrier layer which is less than a height of the softly abrasive loops.

19. The wound cleansing device according to claim 1, whereby the stitchbonded structure of the intermeshed loop fiber system has one of the following knitting patterns: warp knitting, tricot or atlas.

20. The wound cleansing device according to claim 7, whereby the liquid absorbing layer is arranged on an opposite side of the carrier layer with regard to the loop system.

21. The wound cleansing device according to claim 1, wherein the highly abrasive loops and the softly abrasive loops are arranged one-by-one side-by-side in an alternating manner.

22. The wound cleansing device according to claim 5, wherein the natural fibers are cellulose fibers comprising cotton fibers, the semi-synthetic fibers comprise viscose fibers or acetate fibers, and the synthetic fibers are made from a polymer selected from polyester, polyacrylonitrile (PAN), polyethylene, polypropylene or polyamide.

23. The wound cleansing device of claim 19, wherein the intermeshed loop fiber system has a rib or square optic.

* * * * *